United States Patent [19]

Bradshaw

[11] 4,149,548
[45] Apr. 17, 1979

[54] THERAPEUTIC CIGARETTE-SUBSTITUTE

[76] Inventor: John C. Bradshaw, 10 Stevens St., Benardsville, N.J. 07924

[21] Appl. No.: 944,255

[22] Filed: Sep. 21, 1978

[51] Int. Cl.² .......................... A24F 47/00; F24J 1/00; A61F 7/00; A61F 7/12
[52] U.S. Cl. ................. 131/170 A; 126/263; 426/132; 426/134; 128/255; 128/401
[58] Field of Search .................. 126/263; 44/3 R, 3 A; 426/132, 134, 107; 128/212, 208, 401, 255; 266/219; 131/8 A, 171 A, 170 A; 252/70

[56] References Cited

U.S. PATENT DOCUMENTS

| 2,590,931 | 4/1952 | Cabaniss | 126/263 X |
|---|---|---|---|
| 3,182,653 | 5/1965 | Mavleos et al. | 126/204 |
| 3,200,819 | 8/1965 | Gilbert | 128/208 |
| 3,258,015 | 6/1966 | Ellis et al. | 131/8 A |
| 3,347,231 | 10/1967 | Chang | 128/208 |
| 4,036,224 | 7/1977 | Choporis et al. | 128/212 |

Primary Examiner—Robert W. Michell
Assistant Examiner—V. Millin

[57] ABSTRACT

In a preferred embodiment, there is provided an elongated article having a simulated-appearance of a cigarette but being a chemically-resistant chewable plastic having each of opposite ends thereof coated with an edible material preferably inclusive of a tobacco flavor-imparting composition and preferably inclusive further of caffeine, and an intermediate portion of the elongated article having therein isolated adjacent enclosure spaces separated from one-another by a rupturable septum rupturable by application of stress to said article, having sodium hydroxide in one of the enclosure spaces and having hydrochloric acid in the other of the enclosure spaces in amounts and proportions and concentrations sufficient to produce water and heat sufficient to heat the oppositely-coated ends of the elongated article when the septum is ruptured.

14 Claims, 5 Drawing Figures

THERAPEUTIC CIGARETTE-SUBSTITUTE

This invention relates to a cigarette substitute.

BACKGROUND TO THE INVENTION

While the entire physiologic effects of the contents of smoking tobacco of cigarettes and the like, is not fully known nor understood by scientists, it is recognized that at least to some extent there is a psychological dependence upon the physical cigarette as handle, seen and held in the mouth of the smoker, as well as some stimulation obtained from substance(s) such as caffeine. It is fully established beyond any reasonable doubt, however, that the inhaled smoke from smoked cigarettes is seriously hazardous to health of the smoker at least on a long-term basis, and most smoker tend to be long term smokers.

In recognition of the hazardous effects of cigarettes on health, prior patents have been directed toward the concept of replacing the conventional cigarette with a less-hazardous substitute, such as the U.S. Pat. No. 3,200,819 directed to an electrically-heated simulated cigarette providing moistened and flavored air provided to be sucked into the mouth of the would-be smoker. Likewise, U.S. Pat. No. 3,258,015 is directed to a mouthpiece passage and the providing of tobacco-released nicotine carried in water vapor in a heated-state, optionally also including materials such as flavors of essential oils of orange, lemon, mandarin, etc.. The U.S. Pat. No. 3,347,231 discloses a simulated cigarette for sucking into the mouth vapors of aromatic or medicinal material vaporizable upon fracture of a contained ampoule within the simulated cigarette.

THE INVENTION

Broadly, objects of the present invention include the overcoming of difficulties and disadvantages of actual smoking, together with the hazards of actual cigarette smoking being avoided, and the achieving of novel advantages not heretofore available.

Another object is to avoid the need for matches and burning matter that always presents a fire hazard in the prior use of conventional cigarettes or substitute cigarettes using still the burning of matter to produce heat.

Another object is to produce simulated cigarette burn and heat therefrom by chemical means, together with use of chemical means producible of a non-toxic by-product, thereby providing for safe disposal of the discarded used simulated cigarettes of the present invention, as well as elimination of hazard during use.

Another object is to obtain a safe stimulating simulated cigarette smoke devoid of potentially harmful inhailing or sucking-in of various vapors or the like into the lungs.

Another object is to obtain a cigarette substitute in the nature of a simulated cigarette having both the appearance and feel attributes of a real cigarette.

Other objects become apparent from the preceding and followdisclosure.

One or more objects of the present invention are obtained by the embodiments illustrated herein for the sole purpose of improving understanding of the invention together with the setting-forth or preferred embodiments thereof, the scope of the invention not being intended to be unduly limited by the mere examples thereof set-forth in the illustrations, the scope of the invention including various substituted equivalents and variations and modifications within the ordinary skill of the art relative to the disclosed invention.

Broadly the invention may be described as a simulated cigarette device, or alternatively a candy device, which includes an elongated article having therein chemical-containing adjacent compartments separated by a rupturable septum, in which the chemicals are such that upon reaction with one-another an exothermic reaction takes place producing heat sufficient to heat the mouth-end of the elongated articles outer surface which end outer surface is coated with (or the equivalent, impregnated with) an edible material such as either real or artificial tobacco-flavor oils or oils of lemon, lime, vanilla, coffee, peppermint, or with edibles such as chocolate, snuff, chewing tobacco, or any of various artificial flavor materials, but especially preferably including edible matter such as stimulants, preferably caffeine.

Preferably the adjacent compartments are two enclosure spaces located and positioned spaced-away-from the coated end thereof in order to have the chemicals removed from potential placing of that portion of the article into the smoker's (simulated-smoker's) mouth. For the same reason, preferably each of opposite ends are coated with the edible material, while the compartments are located intermediately between the opposite ends, as well as twice the potential enjoyment being available by use of two coated ends, as compared to solely one-end thereof being coated. In such article, there is preferably included an interior heat-conductive structure and mechanism thereof, positioned in heat-transfer contact with the one-or more coated ends such that heat produced upon rupture of the septum is conducted to the edible coating(s).

As in a preferred embodiment employing chemicals of a corrosive nature, namely sodium hydroxide water solution in one compartment and water solution of hydrochloric acid in properly proportioned amounts and concentrations thereof for a one-to-one reaction to produce a corresponding unit of water together with the released exothermic heat of reaction, the walls of the enclosing compartments are of a chemically-resistant material, preferably of a chemically-resistant plastic such as polytetrafluoroethylene (fluroteflon) or polyisobutylethylene, for example; however, other such plastics may be utilized, as well as non-plastics such as fragile glass embodied within protective plastic. Also, the compartments may be of one plastic embodied within another plastic, or the like. It is possible and contemplated to use other chemicals for reaction, including non-corrosive chemicals such as a conventional exothermic hydrophilic material in one compartment and water in another compartment, which upon rupture of the septum reacts to releas heat.

In a preferred embodiment, each or either end of the elongated article has an additional water-containing enclosure as the interior heat-conductive structure and mechanism.

The embodiments having corrosive chemicals noted-above, must have the enclosure walls of a substantially rupture-proof thickness and composition, i.e. they must be substantially non-rupturable walls to thereby prevent accidental release thereof.

While the outer surface of the elongated article may be of varying compositions, with the ends thereof coated with the edible matter as noted above, the coated as well as the chemical-containing outer portions optionally, are coated with a non-toxic plastic of a chewable nature such as nylon-plastic film, or polypropylene, or other conventional non-toxic materials such as various non-toxic latexes or the like.

Other chemically-resistant plastics include typically various polyacrylates or poly-4-methylpentenes.

The invention relates to an article which can be considered preferably a substitute for a cigarette and which will provide some of the psychological satisfaction of cigarette smoking without the health hazards to the user. The invention also can eliminate the inconvenience and nusiance to non-smoker of having to put-up with the offensive smoke from cigarettes being smoked by convention smokers, thus having multiple utility. The use of the present invention is intended to have a therapeutic value in the minimizing of the pain or tensions of past-smokers in the giving-up of the smoking habit, by offering a superior and satisfying alternative. The inventive product is also intended for use by smokers of non-cigarette products such as the dangerous drug materials, to give equivalent satisfaction devoid of health haxards. It is inevitable that the habit of buring tobacco, which seems somehow archaic in the modern technological society, will be replaced someday. The physical, sensory and psychological pleasure of cigarette smoking, however, are less likely to disappear and must be satisfied by something new. This present ivnentive article can go a long way toward satisfying some of these needs in an altered way.

Preferably the invention includes a cylindrical object made substantially of plastic, in the nature described above.

As an example of exothermic heat that typically may be expected, using sodium hydroxide in one enclosure space, and hydrochloric acid in the other, 2.5 molar solution of each, with each being at a volume of two milliliters, there will be a twenty degree Centigrade rise in temperature. It is also contemplated that heat-releasable aromatics which thereby vaporize, upon receipt of the necessary heat, to produce desired aroma, using any conventional or other such aromatic.

The invention may be better understood by making reference to the following Figures.

THE FIGURES

Figure 2:
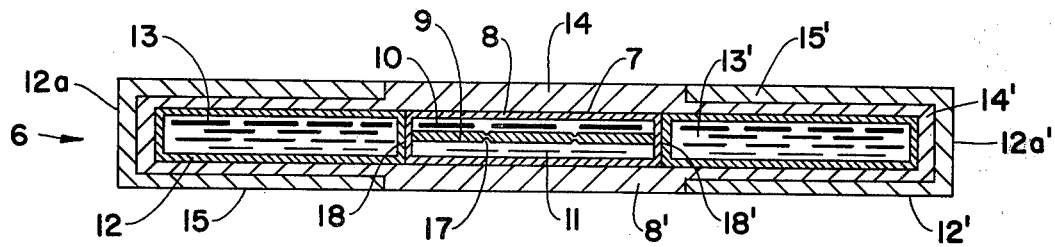
FIG. 2 is a cross-sectional view as taken along line 2—2 of FIG. 1.
Figure 4:
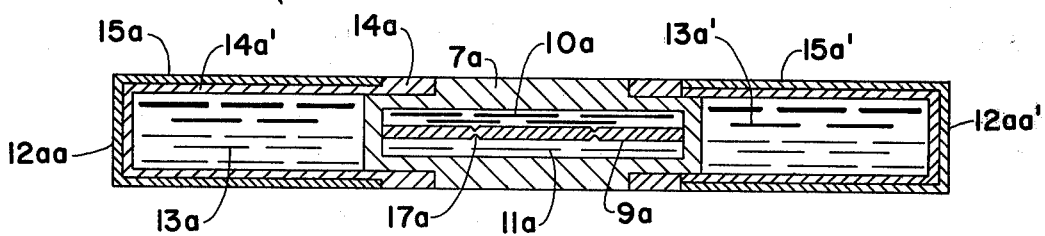
Figure 5:
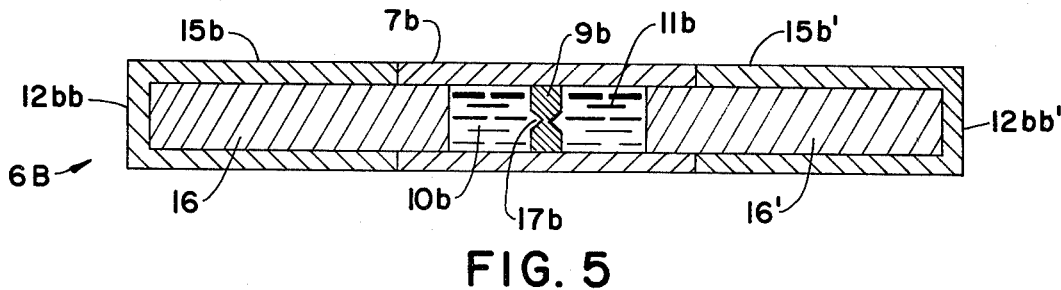

Each of FIGS. 4 and 5 illustrate other alternative embodiments illustrated in side cross-sectional view the same as that of FIG. 2.

DETAILED DESCRIPTION OF THE INVENTION

With regard to the septum discussed-above, while any conventional rupture-type membranes may be utilized, it is here contemplated that the septum is a scored-membrane thus having a thin wall along the scored-portion, and that the septum be also of the corrosive-resistant nature earlier discussed when intended for corrosive chemicals such as sodium hydroxide water solution and hydrochloric acid water solution, for example. On the other hand, any other conventional or desired rupture mechanism may be utilized within the scope of the invention. Upon bending or pressing on the central portion of the present preferred embodiment having the scored membrane, the membrane ruptures because of the fluid pressure thereon or otherwise tearing thereof along the scored portion(s). Thereupon, the exothermic reaction takes place with the resulting heating of the end(s) coated with the edible material.

Figure 1:
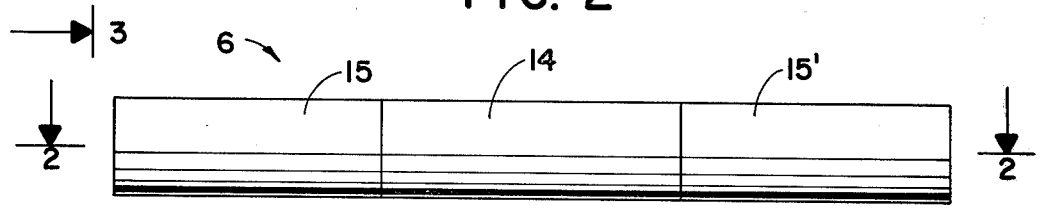
FIG. 1 illustrates a side elevation view of a preferred embodiment of the invention.
Figure 3:
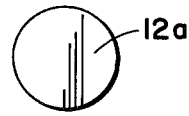
FIG. 3 is an elevation end view as taken along line 3—3 of FIG. 1.

Accordingly, reference may be made to the preferred embodiment of FIGS. 1 through 3. It should be noted that the end views of of the embodiments of FIGS. 4 and 5 are the same as the FIG. 3 view of the FIG. 1 embodiment, and likewise the side view of the embodiments of FIGS. 4 and 5 are the same as the side view of the FIG. 1 embodiment, but of course may be varied as desired.

For the corresponding parts of the embodiments of FIGS. 4, 5, corresponding "prime" or lettered otherwise-same indicia are used as those shown in the embodiment of FIGS. 1 through 3.

Thus, with regard to the embodiment of FIGS. 1 through 3, there is disclosed the simulated cigatette 6 having dual-compartment structure 7 divided into separate container spaces of the enclosures 8 and 8' by the septum 9 having scored portions 17 adapted to rupture when subjected to stress, with a water solution of hydrochloric acid 10 in enclosure 8 and a water solution of sodium hydroxide 11 in enclosure 8'. Opposite ends thereof are adheared by adhesive layers 18 and 18' respectively to the water-containing vessels 12 and 12' containing water 13 and 13' respectively, for thereby intimate contact for heat conductance into the water. The dual-compartment structure 7 and the joined enclosure vessels 12 and 12' are enclosed within plastic 14 having thin ends 14' coated with edible material 15 and 15' respectively. The flat ends 12a and 12a' are identified for purposes of illustration in the FIG. 3 view.

The embodiments of FIGS. 4 and 5 differ principally in the nature of the make-up of the article, suggesting different mechanisms of attachment of the heat-conductive and edible material-coated ends to the intermediate dual-compartment structure, such as male and female mating relationships, facilitating and simplyfying the manufacture thereof. However, additionally the FIG. 5 embodiment illustrates the use of a metal 16 rather than the FIGS. 2 and 4 use of water, as the heat-conductive material, and typically may be copper or other hight heat-conductive metal.

The reactive chemical(s) may be present when the parts are assembled, or alternatively may be injected thereinto as by use of a hypodermic needle or the like. Also, the FIG. 5 embodiment illustrates an alternative arrangement for the septum, extending transversely of the longitudinal axis of the elongated cigarette simulating article of the present invention.

Accordingly, the invention may be characteriaed as hereafter claimed.

I claim:

1. A simulated cigarette device comprising in combination: an elongated article having compartment space formed therein divided into at-least two enclosure spaces separated from one-another by a rupturable septum adapted to rupture when subjected to stress, a first chemical being contained within one of the two enclosure spaces and a second chemical being enclosed within a remaining second one of the two enclosure spaces, the first chemical and the second chemical being such that when admixed, an exothermic reaction takes place producable of heat; and at-least one end of the elongated article being coated by an edible substance.

2. A simulated cigarette device of claim 1, in which said one and said remaining second one of the two enclosure spaces are positioned at a location spaced-away-from said one end.

3. A simulated cigarette device of claim 2, in which said one end includes interior heat-conductive structure in heat-transfer contact with said one and said second one of the two enclosure spaces such that heat is conducted to said one end and said edible substance when said septum is ruptured sufficiently for said first and second chemicals to mix and react.

4. A simulated cigarette device of claim 3, in which said elongated article includes chemically-resistant and substantially non-rupturable walls forming said one and said remaining second one of the two enclosure spaces.

5. A simulated cigarette device of claim 4, including a chewable substantially non-rupturable plastic as an outer surface of said article and on which said edible substance is coated at said one end.

6. A simulated cigarette device of claim 5, in which said heat-conductive structure comprises liquid-enclosure structure having a consumable liquid therein.

7. A simulated cigarette device of claim 6, in which said consumable liquid comprises substantially water.

8. A simulated cigarette device of claim 7, in which both said one end and an opposite end of said elongated article are coated by said edible substance.

9. A simulated cigarette device of claim 8, in which said edible substances is substantially caffeine.

10. A simulated cigarette device of claim 9, in which said edible substance is inclusive of a tobacco flavor-imparting composition.

11. A simulated cigarette device of claim 8, in which said edible substance is inclusive of a flavor-imparting composition.

12. A simulated cigarette device of claim 1, in which said edible substance is inclusive of caffeine.

13. A simulated cigarette device of claim 1, in which said edible substance is inclusive of a flavor-imparting composition.

14. A simulated cigarette device of claim 1, in which said edible substance is inclusive of caffeine and of tobacco flavor-imparting composition.

* * * * *